US00PP32705P2

(12) United States Plant Patent

Fernandez et al.

(10) Patent No.: US PP32,705 P2

(45) Date of Patent: Dec. 29, 2020

(54) STRAWBERRY PLANT NAMED 'NCS 10-038'

(50) Latin Name: ***Fragaria* x *ananassa* Duchense**
Varietal Denomination: NCS 10-038

(71) Applicant: North Carolina State University, Raleigh, NC (US)

(72) Inventors: Gina E. Fernandez, Raleigh, NC (US); Jeremy Pattison, Raleigh, NC (US); James R. Ballington, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 16/602,013

(22) Filed: Jul. 19, 2019

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208, 209
CPC ..... A01H 5/0893; A01H 5/08; A01H 5/00; A01H 6/74; A01H 6/7409
See application file for complete search history.

(56) References Cited

PUBLICATIONS

Fernandez See NC State Univeristy Breeding Lines as Expo Field Tour, retrieved on Mar. 9, 2020, posted on Nov. 2, 2016 at https://strawberries.ces.ncsu.edu/2016/11/see-nc-state-university-breeding-lines-at-expo-field-tour/, 4 pp. (Year: 2016).*
Fernandez et al., NC State University Strawberry Breeding Program2015 Yield Trials, Future Projects and Grower Feedback, 121 pages.
Fernandez et al., NC State University Strawberry Breeding Progarm2015-16 Yield Trials, Grower Feedback and Future Research, 2016, 73 pages.
Fernandez et al., NC State University Strawberry Breeding Program: Southeast Regional Fruit and Vegetable Conference, Jan. 2017, 54 pages.
Fernandez et al,, Promising new selections in the NC State University Strawberry Breeding Program, Strawberry presentation Clemson 2015, 32 pages.
Fernandez et al., Promising new selections in the NC State University Strawberry Breeding Program, Expo 2014, 43 pages.
Fernandez, Gina, NC State University Strawberry Breeding Program Update, Nov. 2017, 36 pages.
Fernandez, Gina, Strawberry Grower, North Carolina Strawberry Association, Apr. 2016, 16 pages specifically pp. 1-2.
Fernandez et al. Breeding Strawberries for North Carolina and the Southern US. The Strawberry Grower, Mar. 2015 , 16 pages, specifically pp. 4-5.
Perkins, Veazie et al. "Fruit Quality and Composition of Two Advanced North Carolina Strawberry Selections" 16 (S1):220-227 2016.

* cited by examiner

*Primary Examiner* — June Hwu
(74) *Attorney, Agent, or Firm* — Myers Bigel, P.A.

(57) ABSTRACT

A new and distinct variety of commercial strawberry plant (*Fragaria* x *ananassa* Duchense) named 'NCS 10-038' substantially as illustrated and described, characterized by its very high yields, mid-season (peak harvest weeks 15-18) fruit ripening with the fruit having a medium size, good flavor, conical to wedge shape, and being of a good quality with very good flesh firmness and good skin toughness. 'NCS 10-038' has fair to good firmness and is suitable for pick your own and local sales.

3 Drawing Sheets

Latin name of the genus and species: The Latin name of the novel strawberry plant disclosed herein is *Fragaria* x *ananassa* Duchense.

Variety denomination: The inventive strawberry variety has been given the variety denomination 'NCS 10-038.'

BACKGROUND OF THE INVENTION

The present invention relates to a new and distinct variety of strawberry (*Fragaria* x *ananassa* Duchense) named 'NCS 10-038'. This strawberry plant (genotype) originated in a strawberry breeding plot in Salisbury, N.C. The genotype was collected from open pollinated fruit from the seed parent 'NCH 08-07'. The seed parent is an unreleased breeding selection with med large size, high fruit quality and good appearance. The seeds collected from the female parent in the spring of 2009 were germinated in the summer and planted in the fall of 2009. The selection was made in the spring of 2010. 'NCS 10-038' was first asexually propagated at the Piedmont Research Station, Salisbury N.C., Rowan County, in 2011. Ten daughter plants were propagated from runner tips originating from the mother plant and transplanted to second test trials where they were compared to several other genotypes in 2011. Plants were propagated in subsequent years and were established in replicated trials in 2012-17. 'NCS 10-038' exhibited very high yields through the season in trials in multiple locations and years. Propagules of 'NCS 10-038' in all trials have been identical to the initial daughter plants. The combination of traits disclosed herein that characterize 'NCS 10-038' have been retained true to type through successive cycles of asexual propagation.

SUMMARY OF THE INVENTION

'NCS 10-038' when grown in the piedmont regions of North Carolina has produced consistently high yields (Tables 1 and 2). Yields are typically 130-150% higher than 'Chandler', the current standard cultivar grown in North Carolina. At the Central Crops Research Station, in Clayton N.C., flowering occurred in 2016 in weeks 10-16. Peak ripe fruit yield occurred in weeks 15-18. The new and distinct variety of strawberry *Fragaria* x *ananassa* Duchense 'NCS 10-038' has the following unique combination of desirable features that are outstanding in a new variety including (1) very high yield, (2) long season of harvest for spring crop, (3) semi-firm fruit, and (4) adapted to the southeastern US. 'NCS 10-038' is suitable for pick your own and local sales.

BRIEF DESCRIPTION OF THE DRAWINGS

The accompanying photographs show typical specimens of 'NCS10-038'. The photographs were taken in Clayton, N.C.

DETAILED BOTANICAL DESCRIPTION

Figure 1:
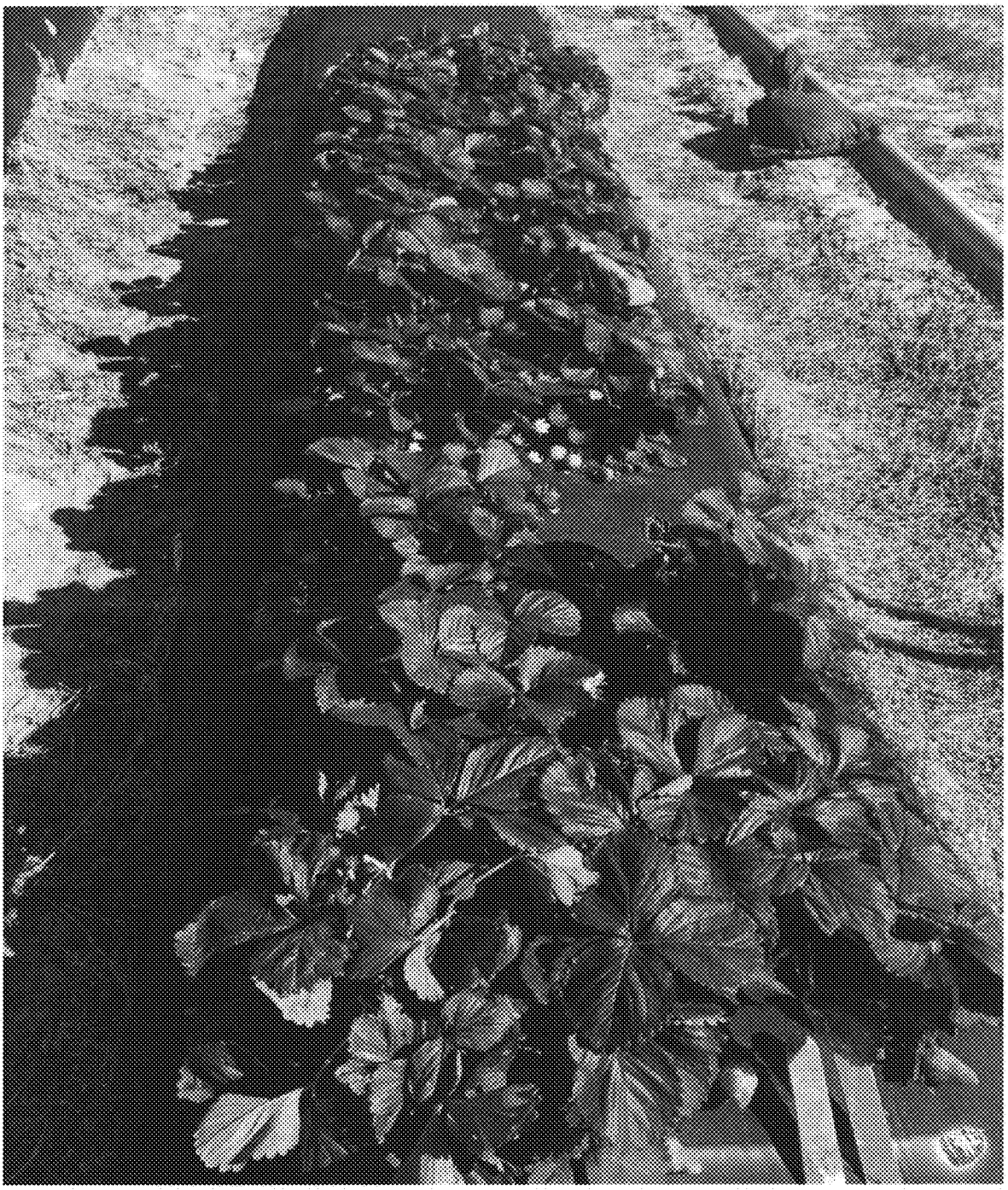
FIG. 1 shows whole 8-month old plants of 'NCS 10-038' including leaves, inflorescences and fruit at varying stages of ripeness.
Figure 2:
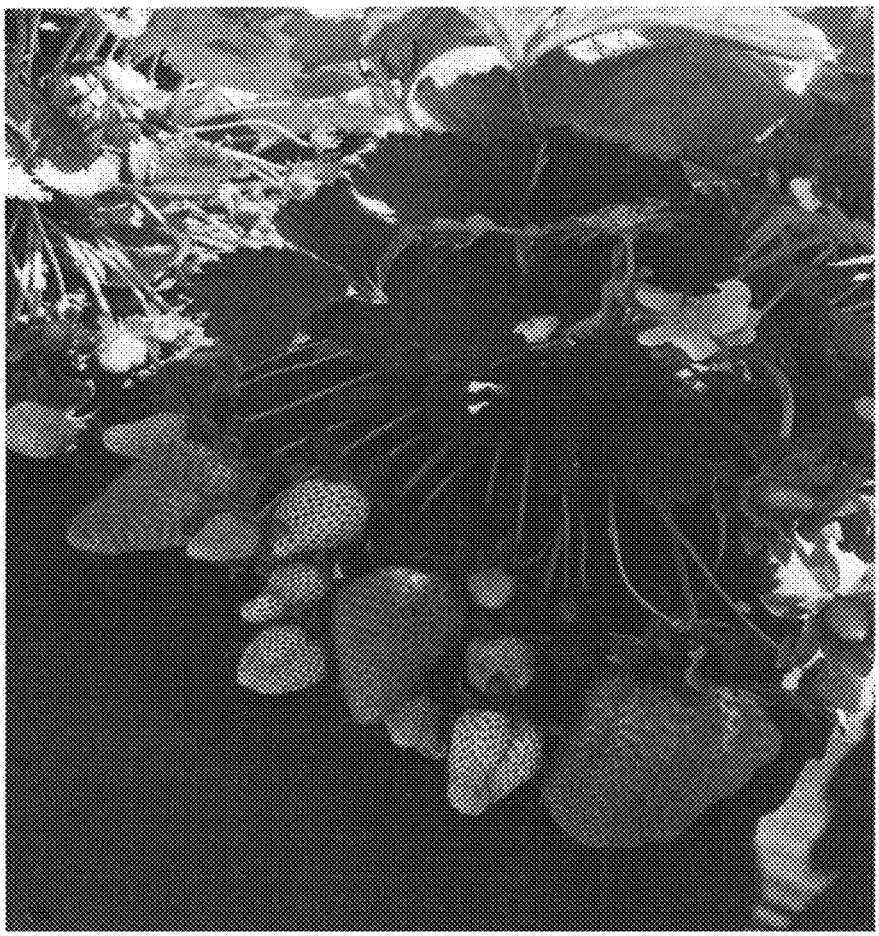
FIG. 2 shows a close up of a single 8 month old plant of 'NCS 10-038' showing leaves, inflorescences and fruit at varying stages of ripeness.
Figure 3:
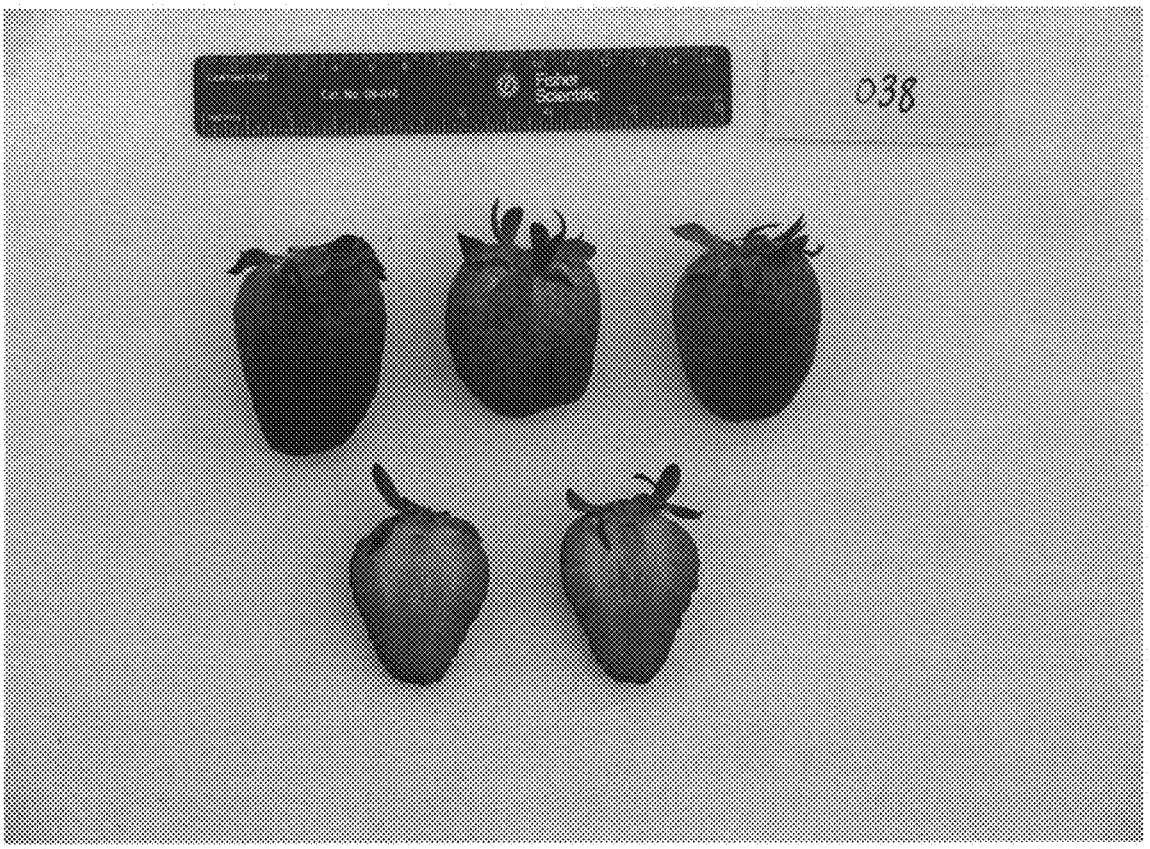
FIG. 3 shows a close-up of fruit of 'NCS 10-038', sliced and whole. The designation of "038" in FIG. 3 is an abbreviation for the claimed plant, 'NCS 10-038'.

The following is a detailed description of a new distinct strawberry variety known as 'NCS 10-038'. The description is based on observations taken from the 2014-2017 growing seasons in the two piedmont locations of Clayton and Salisbury, N.C. Each year the plants are set in the fall and fruiting occurs in the following spring. This description is in accordance with International Union for the Protection of New Varieties of Plants (UPOV) terminology. Color designations and descriptions and other phenotypical traits may deviate from the stated values depending on location and season as this genotype has not been observed in all environmental conditions. Color terminologies are based on The Royal Horticultural Society Colour Chart, London (R.H.S.) ($5^{th}$ Edition. 2007).

Plant:

*Average height.*—29.3 cm.
*Average width.*—19 cm.
*Canopy density.*—Moderate.
*Growth habit.*—Semi erect to erect.
*Number of crowns/plant.*—5-13.
*At peak production, the plant will have multiple crowns. Each crown will produce one truss and each truss will have several fruit.*
*Vigor.*—Moderate.

Leaf:

*Overall.*—Pinnately compound with 3 leaflets.
*Mean length including petiole.*—301 mm.
*Mean width.*—178 mm.

Terminal leaflet:

*Upper leaf surface color.*—137B.
*Lower leaf surface color.*—138B.
*Terminal leaflet length.*—87 mm.
*Terminal leaflet width.*—88 mm.
*Length to width ratio.*—0.99.
*Shape in cross section.*—Concave.
*Leaflet shape.*—Obovate.
*Terminal leaflet serration number.*—18.
*Terminal leaflet margin profile.*—Obtuse.
*Terminal leaflet shape of base.*—Acute cuneate.
*Terminal leaflet shape of serrations.*—Pointed.
*Interveinal blistering.*—Moderate.
*Pubescence density of leaves, lower surface.*—Sparse.
*Leaf glossiness.*—Semi-glossy.
*Venation pattern.*—Pinnate.
*Petiole.*—Petiole length — 23.1 mm. Petiole diameter — 2.3 mm. Pubescence density of petiole — Moderate. Petiole pose of hairs — Perpendicular. Petiole color — 144C. Anthocyanin — Present.
*Petiolule.*—Length — terminal 3.5 mm, lateral 2.0 mm, diameter 1.2 mm. Color — 144C.
*Stipule.*—Stipule length — 28.0 mm. Stipule width — 8.5 mm. Stipule color — 145B. Stipule pubescence — Yes. Anthocyanin — No. Bract pair or single — Mostly single, occasionally paired.

Secondary leaflets:

*Color upper surface.*—137B.
*Color lower surface.*—138B.
*Secondary leaflet length.*—85 mm.
*Secondary leaflet width.*—86 mm.
*Length to width ratio.*—0.98.
*Shape in cross section.*—Concave.
*Leaflet shape.*—Obovate.
*Secondary leaflet margin profile.*—Obtuse.
*Secondary leaflet shape of base.*—Oblique.
*Secondary leaflet shape of serrations.*—Pointed.
*Pubescence density.*—Leaves, lower surface — Sparse.
*Number of leaflet serrations.*—17.
*Leaf glossiness.*—Semi-gloss.
*Texture.*—Moderately smooth.
*Venation pattern.*—Pinnate.

Stolons:

*Number of daughter plants.*—25-40 depending on environmental conditions.
*Anthocyanin.*—Variable, absent to moderate.
*Thickness.*—3 mm.
*Pubescence.*—Very sparse nearly glabrous.

Inflorescence:

*Time of flowering.*—Short day flowering habit.
*Position relative to canopy.*—At or below canopy.
*Branching of the inflorescence.*—At or close to crown.
*Number of flowers/inflorescence.*—6.
*Relative flower size.*—Medium.
*Relative calyx size to corolla.*—< to =.
*Inflorescence attitude at harvest.*—Mostly decumbent.
*Inflorescence length.*—20 cm.
*Flower diameter.*—39.4 mm.
*Calyx diameter.*—40 mm.
*Blossom longevity.*—1-2 days.
*Number of stamens.*—Average of 30.
*Anther color.*—13A to 16A.
*Filament color.*—150C.
*Style color.*—150A.
*Stigma color.*—2D.
*Petals.*—Petal length — 14.9 mm. Petal width — 14.5 mm. Petal size ratio — 1.02. Petals/flower — 5. Petal color — 155D. Corolla diameter — 40 mm. Flower shape — Orbicular. Number flowers/inflorescence — 3-6. Petal spacing — Even to overlapping.
*Sepals.*—Sepal number — 11. Sepal color — 137A. Sepal length — 16.2 mm. Sepal width — 7.85 mm. Sepal attitude — outward, some upward.

*Calyx*.—Calyx color — 137A. Corolla diameter — 39.3 mm. Calyx size compared to fruit — > or =. Calyx attachment — level.

*Pedicels*.—Pedicel Color — 145A. Pubescence — low. Mean length of the pedicel attached to the primary fruit — 55 mm.

Fruit:

*Fruit fragrance*.—Moderate.

*Flavor*.—Moderate flavor.

*Fruit skin color*.—53A.

*Fruit flesh color*.—47A.

*Evenness of color*.—Outside skin even, inside from 47A in the apex to NN155C in the center near the calyx.

*Flesh and skin firmness at full ripe stage*.—Moderately firm (See Table 3).

*Rain damage*.—Minimal.

*Fruit size average*.—16.4-17.5 g.

*Fruit shape*.—Conical to slight wedge.

*Fruit length*.—41.1 mm.

*Fruit width*.—34.8 mm.

*Fruit length to width ratio*.—1.18.

*Fruit skin glossiness*.—Glossy.

*Fruit calyx orientation*.—Flat to slight rise.

*Band without achenes*.—None.

*Center cavity size*.—None or very small 2-3 mm.

*Unevenness of surface*.—Even.

*Disease resistance*.—Susceptible to grey mold (*Botrytis cinerea*) and anthracnose fruit rot (*Colletotrichum acutatum*).

Seeds:

*Achene color*.—151A to 53A, achene color individually present depending on location on the fruit.

*Achene attachment*.—Even with surface.

*Achene shape*.—Oval.

Preferred planting date is about 25 September in Salisbury, N.C. and October 5 in Clayton, N.C. Nursery performance has been fair in western NC locations due to moderate production of many runners that produce multiple daughter plants that root easily.

The technical (pomological) descriptive data comparing yield of 'NCS 10-038' to that of 'Sweet Charlie' (U.S. Plant Pat. No. 8,729), 'Camarosa' (U.S. Plant Pat. No. 8,708) and 'Chandler' (U.S. Plant Pat. No. 5,262) in Salisbury, N.C. and in Clayton, N.C. is presented in Tables 1-2. The post-harvest storage life attributes comparing 'NCS 10-038' to 'Camarosa' and 'Chandler' as well as 'NCS10-156' are presented in Tables 3-4. This data was previously published in part in Perkins-Veazie, P., J. Pattison, G. E. Fernandez and G. Ma. 2016. Fruit Quality and Composition of Two Advanced North Carolina Strawberry Selections. *Intl. J. Fruit Science*. 16:(Sup 1): 220-227).

TABLE 1

Piedmont Research Station, Salisbury NC. 2015-16
Total yield, marketable yield, percent marketable yield and average berry weight.

| Genotype | Total Yield (g/plant) | Total Yield (lbs/A) | Marketable Yield (g/plant) | Marketable Yield (lbs/A) |
|---|---|---|---|---|
| NCS 10-038 | 931 | 35749 | 771 | 29605 |
| NCS 10-156* | 697 | 26757 | 586 | 22484 |
| Camarosa | 637 | 24431 | 550 | 21107 |
| Chandler | 665 | 25505 | 505 | 19389 |
| Sweet Charlie | 488 | 18712 | 406 | 15592 |

TABLE 1-continued

Piedmont Research Station, Salisbury NC. 2015-16
Total yield, marketable yield, percent marketable yield and average berry weight.

| Genotype | Percentage Marketable Yield (% of total) | Marketable Percent of Chandler | Average Berry weight (g) |
|---|---|---|---|
| NCS 10-038 | 82.8 | 153 | 16.4 |
| NCS 10-156* | 84.0 | 116 | 18.9 |
| Camarosa | 86.4 | 109 | 21.7 |
| Chandler | 76.0 | 100 | 16.9 |
| Sweet Charlie | 83.3 | 80 | 17.3 |

*'NCS 10-156' is co-pending Plant Pat. Application No. 16/602,017

TABLE 2

Central Crops Research Station, Clayton, NC 2015-16
Total yield, marketable yield, percent marketable yield and average berry weight.

| Genotype | Total Yield (g/plant) | Total Yield (lbs/A) | Marketable Yield (g/plant) | Marketable Yield (lbs/A) |
|---|---|---|---|---|
| NCS 10-038 | 785 | 30131 | 712 | 27309 |
| Camarosa | 668 | 25619 | 607 | 23290 |
| Chandler | 669 | 25690 | 539 | 20698 |
| NCS 10-156* | 558 | 21400 | 485 | 18603 |
| Sweet Charlie | 337 | 12941 | 306 | 11725 |

| Genotype | Percentage Marketable Yield (% of total) | Marketable Percent of Chandler | Average Berry weight (g) |
|---|---|---|---|
| NCS 10-038 | 90.6 | 132 | 17.5 |
| Camarosa | 90.9 | 113 | 18.2 |
| Chandler | 80.6 | 100 | 19.8 |
| NCS 10-156* | 86.9 | 90 | 14.6 |
| Sweet Charlie | 90.6 | 57 | 14.2 |

*'NCS 10-156' is co-pending Plant Pat. Application No. 16/602,017

TABLE 3

Subjective ratings of strawberry fruit held at 4 C for 8 days averaged for 2014 and 2015 seasons[z].

| Selection | Overall appearance[y] | Fruit shrivel | Fruit darkness | Calyx brown | Calyx shrivel | Fruit firmness | Berries with mold (%) |
|---|---|---|---|---|---|---|---|
| Camarosa | 3.8a | 3.9ab | 3.7bc | 3.8a | 3.6a | 4.3a | 3.1a |
| Chandler | 4.0a | 4.3a | 3.8b | 3.9a | 3.8a | 3.2b | 4.6ab |
| NCS 10-038 | 4.0a | 4.4a | 4.2a | 3.4a | 3.6a | 3.8b | 6.1ab |
| NCS 10-156 | 3.3b | 3.3b | 3.2c | 3.0b | 3.0a | 2.2c | 12.3b |

[z]All fruit quality attributes were given subjective ratings of 1 to 5 where a higher number indicates better fruit quality. Berries with mold was determined by 100% × (no. berries with mold/total no. berries).

[y]Means within column with same letter indicate no significant difference using Tukey's HSD, $p < 0.05$.

TABLE 4

Fruit composition of fully ripe freshly harvested strawberry selections grown in Salisbury, NC in 2014 and 2015[z].

| Selection | SSC (%) | pH | Titratable acidity (TA) (% as citric acid) | SSC/TA | Total antho-cyanin (mg P3G/100 g fwt)[y] | Total phenolic content (mg GA/100 g) |
|---|---|---|---|---|---|---|
| Day 0 | | | | | | |
| Camarosa | 7.1b | 3.82a | 0.69b | 10.6ab | 41.27a | 155.62a |
| Chandler | 6.8b | 3.71b | 0.69b | 10.0ab | 48.55a | 157.57a |
| NCS 10-038 | 7.1b | 3.67b | 0.75a | 9.8b | 28.87b | 142.05b |
| NCS 10-156 | 7.8a | 3.78a | 0.72ab | 11.0a | 33.95ab | 152.23a |
| Day 8 | | | | | | |
| Camarosa | 7.6b | 3.97a | 0.64b | 12.1a | 51.52a | 152.16bc |
| Chandler | 7.6b | 3.87b | 0.66b | 11.6a | 45.39ab | 158.50a |

TABLE 4-continued

Fruit composition of fully ripe freshly harvested strawberry selections grown in Salisbury, NC in 2014 and 2015[z].

| Selection | SSC (%) | pH | Titratable acidity (TA) (% as citric acid) | SSC/TA | Total antho-cyanin (mg P3G/100 g fwt)[y] | Total phenolic content (mg GA/100 g) |
|---|---|---|---|---|---|---|
| NCS 10-038 | 6.9c | 3.81b | 0.68b | 10.2b | 29.86c | 147.59c |
| NCS 10-156 | 8.7a | 3.87b | 0.77a | 11.6a | 37.04b | 153.21b |

[z]Each selection consists of a mean of 3 to 7 samples, representing 3 harvest dates per year. Means within column with same letter indicate no significant difference using Tukey's HSD, $p < 0.05$.
[y]P3G and GA are pelargonidin 3-glucoside and gallic acid equivalents, respectively.

That which is claimed is:

1. A new and distinct variety of *Fragaria* x *ananassa* Duch. plant named 'NCS 10-038', substantially as described and illustrated herein.

* * * * *